United States Patent [19]

Burke et al.

[11] Patent Number: 5,292,502
[45] Date of Patent: Mar. 8, 1994

[54] NON-IRRITATING DENTIFRICE

[75] Inventors: Michael R. Burke, Somerset; Michael Prencipe, East Windsor; James M. Buchanan, Mercerville, all of N.J.

[73] Assignee: Colgate-Palmolive Co., Piscataway, N.J.

[21] Appl. No.: 908,104

[22] Filed: Jul. 2, 1992

[51] Int. Cl.$^5$ ............ A61K 7/16; A61K 7/18; A61K 7/22
[52] U.S. Cl. ............................ 424/54; 424/49; 424/52; 424/57
[58] Field of Search ..................... 424/49–58

[56] References Cited

U.S. PATENT DOCUMENTS

| | | | |
|---|---|---|---|
| 3,696,192 | 10/1972 | Embring | 424/55 |
| 3,954,962 | 5/1976 | Prussin | 424/49 |
| 3,957,967 | 5/1976 | L'Orange | 424/49 |
| 4,391,798 | 7/1983 | Tavss et al. | 424/52 |
| 4,405,599 | 9/1983 | Smigel | 424/53 |
| 4,603,045 | 7/1986 | Smigel | 424/52 |
| 5,000,939 | 3/1991 | Dring et al. | 424/50 |
| 5,041,280 | 8/1991 | Smigel | 424/52 |

OTHER PUBLICATIONS

Schoenrock et al., CA. 115:282523g (1991) of Ger DE 4007638 Sep. 12, 1991.
Takahashi CA. 112:124914b (1990) of JPN 01211521 Aug. 24, 1989.
Final Report CA. 108:101090h (1988) of J. Am. Coll. Toxicol. 6(3):261–277(1987).
Levi et al., CA. 86:18726b (1977).
Wakeman CA. 83:103158a (1975) of Fr. lemonde 2229389 Dec. 13, 1974.
Schultz CA. 76:76368r (1972) of Amer. Met. Perfume 87(1):29–32 (1972).
Janistyn et al., CA. 74:102992p (1971) of Ger DE 1943441 Mar. 4, 1971.
Embring CA. 73:112987r (1970) of Ger DE 2008694 Feb. 27, 1969.

Primary Examiner—Shep K. Rose

[57] ABSTRACT

An oral composition of acceptable taste substantially non-irritating to oral tissue, the composition containing an effective amount of a sodium lauryl sulfoacetate surfactant purified to contain less than 18% by weight impurities. An amount of a nonionic or amphoteric compound is included in the composition to enhance the foaming ability of the purified sodium lauryl sulfoacetate surfactant as well as to further reduce its irritancy potential.

16 Claims, No Drawings

NON-IRRITATING DENTIFRICE

BACKGROUND OF THE INVENTION

1. Field of the Invention

This invention relates generally to a substantially non-irritating oral composition, and more particularly, to a non-irritating oral composition exhibiting high foaming properties.

2. The Prior Art

Sodium lauryl sulfate (SLS) is a widely used surfactant in oral compositions. Surfactants, and particularly anionic surfactants such as sodium lauryl sulfate (SLS) are an essential ingredient of oral compositions and serve as a solubilizing, dispersing, emulsifying and wetting agent for the other ingredients present in the dentifrice and is especially effective in solubilizing the flavor present. A cosmetic effect of the presence of the surfactant is that it promotes foaming of the oral composition. Oral compositions with strong foaming ability are preferred by consumers since the foaming provides the perception that the oral composition cleans effectively only if it foams well.

The incorporation of anionic surfactants such as SLS in oral compositions such as dentifrices is known to cause adverse reactions to oral tissue as shown in R. C. Caldwell and R. E. Stallard, *A Textbook of Preventive Dentistry*, 196, W. B. Saunders (1977); L. J. Guarnieri, IADR, *Abstract No.* 661 (1974); L. J. Guarnieri, *Thesis*, University of Indiana (1970).

One example is gingival irritation. It is also believed that SLS is responsible for sloughing of the oral mucosa.

The art therefore has been seeking a non-irritating alternative surfactant to SLS as a surfactant for dentifrices.

U.S. Pat. Nos. 4,690,776 and 5,041,280 disclose the use of the anionic surfactant sodium lauryl sulfoacetate in dentifrice formulations. However, the problem of oral irritation due to the presence of anionic surfactants in the dentifrice is not mentioned in the aforesaid patents.

According to the published literature; namely, "Surfactants in Cosmetics (Marcel Dekker), Vol. 16, Ch. 10, Pages 303-304 (1985), sodium lauryl sulfoacetate is of comparatively little importance commercially in oral hygiene products. According to this publication, although the use of sodium lauryl sulfoacetate has been proposed as a foaming agent in dentifrices and other dental preparations, it is not considered as an organoleptically acceptable product for commercial applications.

Attempts to use commercially available sodium lauryl sulfoacetate as a surfactant in oral products such as dentifrices indicate the problem of a bitter taste associated with the presence of the compound in the oral product. Further, compared to SLS, dentifrices employing sodium lauryl sulfoacetate as the surfactant exhibit inferior foaming properties.

SUMMARY OF THE INVENTION

In accordance with the present invention, there is provided a substantially non-irritating oral composition of acceptable taste, the dentifrice containing as the surfactant a purified sodium lauryl sulfoacetate having admixed therewith less than 18% non-dodecyl sodium sulfoacetate impurities. The purified sodium lauryl sulfoacetate, when incorporated in the oral composition in combination with a polymeric foam-enhancing nonionic material such as ethylene oxide containing polymers and oxygen-containing heterocyclic nitrogen compounds or an amphoteric compound, exhibits a further reduction in irritation potential as well as enhanced foaming properties.

It is highly surprising that in contrast to the unpleasant bitter taste of oral compositions containing unpurified sodium lauryl sulfoacetate, those of the present invention containing purified sodium lauryl sulfoacetate are organoleptically pleasing.

DESCRIPTION OF THE PREFERRED EMBODIMENTS

The oral compositions of the present invention are formulated using a purified form of sodium lauryl sulfoacetate as the surfactant. The sodium lauryl sulfoacetate material that is commonly commercially available is not the pure compound dodecyl sodium sulfoacetate represented by the formula:

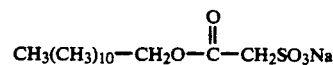

but a mixture of compounds with dodecyl sodium sulfoacetate comprising no more than 70% of the mixture with the remainder being impurities or unreacted products. Thus, as normally employed, the designation or chemical description "sodium lauryl sulfoacetate" to commercially available product refers to a material containing as impurities varying amounts of sodium salts of non-dodecyl sodium sulfoacetates; e.g., sodium sulfoacetate, as well as the predominanting dodecyl sulfoacetate salt. Commercial sodium lauryl sulfoacetate also contains varying amounts of sodium salts of inorganic acids; e.g., sodium chloride and sodium sulfate, as well as feedstock alcohols; namely, unreacted lauryl alcohol.

The present inventors have investigated the organoleptic properties of various forms of material commercially available as "sodium lauryl sulfoacetate", including one form that has recently become available as a purified composition containing about 18% or less by weight impurities. It has been found that purified sodium lauryl sulfoacetate; i.e., sodium lauryl sulfoacetate having combined therewith 18% or less impurities, hereinafter referred to as "purified sodium lauryl sulfoacetate", is organoleptically more pleasing and tastes better than the unpurified sodium lauryl sulfoacetate.

When used as a surfactant ingredient in the preparation of dentifrices and rinses in accordance with the practice of the present invention, the purified sodium lauryl sulfoacetate material must contain less than about 18% impurities based on the weight of the sodium dodecyl sulfoacetate to be considered a useful additive. A preferred material is a purified sodium lauryl sulfoacetate composition having the following analysis:

|  | wt % range |
|---|---|
| dodecyl sodium sulfoacetate | 82.0–85.0 min. |
| sodium chloride | 7.5–8.0 max. |
| sodium sulfate | 7.5–8.0 max. |
| sodium sulfoacetate | <4 max. |
| free alcohol | <0.6–0.8 max. |

The purified sodium lauryl sulfoacetate is incorporated in the oral compositions of the present invention at a concentration of about 0.5 to about 5.0% by weight and preferably about 0.7 to about 2.0% by weight. At these concentrations, the purified sodium lauryl sulfoacetate is unexpectedly found to be organoleptically acceptable, the normal bitter taste associated with unpurified commercial sodium lauryl sulfoacetate being absent when used in oral hygiene products.

Although oral compositions prepared using the purified sodium lauryl sulfoacetate as the surfactant component exhibit inferior foaming properties, the present inventors have discovered that the foaming properties of the oral composition may be enhanced by the inclusion in such composition of nonionic additives such as ethylene oxide containing polymers, and oxygen-containing heterocyclic nitrogen compounds, or amphoteric compounds. The inclusion of the nonionic or amphoteric additives in oral compositions containing purified sodium lauryl sulfoacetate as the surfactant serve to increase the foaming ability of the oral composition to levels desired by consumers and, in addition, further reduce the irritability potential of the purified sodium lauryl sulfoacetate.

Foam enhancing nonionic ethylene oxide containing polymers which may be used in the oral compositions of the present invention include a nonionic water soluble polyoxyethylene monoester of sorbitol with a $C_{10-18}$ fatty acid ester of sorbitol (and sorbitol anhydrides), consisting predominantly of the monoester, condensed with about 50–100, preferably about 60, moles of ethyleneoxide. The fatty acid (aliphatic hydrocarbon-monocarboxylic acid) may be saturated or unsaturated; e.g., lauric, palmitic, stearic, oleic acids. Tween 60 (Trademark) is especially preferred, which is a polyoxyethylene (60) sorbitan monolaurate commercially available from ICI. Other ethylene oxide containing polymers include polyoxyethylene polyoxypropylene block copolymers having the formula $HO(C_2H_4O)_b(C_3H_6O)_a(C_2H_4O)_bH$ wherein a is an integer such that the hydrophobic base represented by $(C_3H_6O)$ has a molecular weight of about 2750 to 4,000, b is an integer such that the hydrophilic moiety represented by $(C_2H_4O)$ constitutes about 70–80% by weight of the copolymer. Block copolymers of this composition are available commercially from BASF under the trademark Pluronic F type.

Pluronic F-108, which has a molecular weight of 3200 and contains 80% of the hydrophilic polyoxyethylene moiety, and Pluronic F-127, which has a molecular weight of 4000 and contains 70% of the hydrophilic polyoxyethylene moiety, are preferred in the practice of the present invention.

Further examples of nonionic ethylene oxide containing polymers useful in the practice of the present invention include poly(ethylene oxide) of the formula $H(OCH_2CH_2)_xOH$ having a molecular weight of 100,000 to 5,000,000. Preferably, the molecular weight of the poly(ethylene oxide) is between 500,000 and 4,000,000. These polymers are available from Union Carbide Corp. as granules of water soluble poly(ethylene oxide) resin under the trademark Polyox. Polyox N-60K, having a molecular weight of 2,000,000 is preferred for use in the practice of the present invention.

The nonionic ethylene oxide containing polymers are incorporated in the oral compositions of the present invention at a concentration of about 0.001 to about 5% by weight and preferably about 0.002 to about 1% by weight.

Nonionic oxygen-containing heterocyclic nitrogen compounds useful in the practice of the present invention include Allantoin (2,5-dioxo-4-imidazolidinyl) urea, alkyl substituted lactams such as dodecyl substituted lactams available from GAF under trademark "Surfadone" and vinyl pyrolidone and polymers thereof such as polyvinyl pyrolidone (PVP).

The oxygen-containing heterocyclic nitrogen compounds are incorporated in the oral compositions of the present invention at a concentration of about 0.001 to about 5% by weight and preferably about 0.002 to about 1% by weight.

Amphoteric compounds useful in the practice of the present invention include betaine compounds having the formula

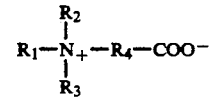

wherein R is an alkyl group having 10 to about 20 carbon atoms, preferably 12 to 16 carbon atoms or the amido radical:

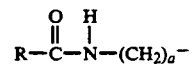

wherein R is an alkyl group having about 10 to 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyl dimethyl betaines include decyl betaine or 2-(N-decyl-N,N-dimethylammonio) acetate, coco betaine or 2-(N-coco N,N-dimethylammonio) acetate, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like. Cocoamidopropyl betaine available from Goldschmidt under the trademark Tegobetaine is preferred in the practice of the present invention.

The amphoteric compounds are incorporated in the oral compositions of the present invention at a concentration of about 0.001 to about 2% by weight and preferably about 0.05 to 1% by weight.

The oral compositions of the present invention may be substantially solid or pasty in character, such as a toothpaste, gel or dental cream. The vehicle of such solid or pasty oral preparations generally contains a polishing material.

Examples of materials useful as polishing agents in the oral composition of the present invention include water-insoluble siliceous polishing agents, hydrated alumina and dicalcium phosphate, including dicalcium phosphate dihydrate and anhydrous dicalcium phosphate. Siliceous polishing agents include colloidal silica xerogel, precipitated silica and sodium aluminosilicates or silica grades containing combined alumina, typically in amount of about 0.1–7% by weight. Other polishing materials include insoluble sodium metaphosphate, calcium carbonate, calcium pyrophosphate, trimagnesium phosphate, magnesium carbonate, etc. Mixtures of polishing agents may be used.

Typically, the polishing material is included in the dentifrice composition of the present invention in an amount of from about 20 to about 60% by weight and preferably from about 35 to about 55%.

The oral compositions of this invention may also contain conventional additional ingredients such as coloring or whitening agents, or preservatives such as sodium benzoate, in amounts of up to 5% by weight and preferably up to 1%, provided they do not interfere with the chemical and cosmetic stability properties of the finished product.

In toothpaste, gel or dental creams, the oral composition is formulated using a water and humectant carrier typically in an amount ranging from about 10 to about 90% of the composition. Sorbitol, typically commercially available in 70% aqueous solution, glycerine, low molecular weight polyethylene glycol (e.g. about 200 to 600) or propylene glycol exemplify humectants/carriers used to formulate the toothpaste, gel or dental compositions.

Toothpastes, creams and gels typically contain a natural or synthetic thickener or gelling agent in proportions of about 0.1 to about 10, preferably about 0.5 to about 5 wt. %. Suitable thickeners include Irish moss, gum tragacanth, starch, hydroxyethypropylcellulose, hydroxybutyl methyl cellulose, hydroxypropyl methyl cellulose, hydroxyethyl cellulose (e.g., available as Natrosol), sodium carboxymethyl cellulose, poly(methyl vinyl ether/maleic anhydride) available for example as Gantrez AN 139 (GAF Corporation), and carboxyvinyl polymer for example available as Carbopol (e.g., 934, 940, 941). These Carbopol products of B. F. Goodrich Co. are described in U.S. Pat. Nos. 2,798,053; 2,923,692 and 2,980,655, being essentially colloidally water-insoluble acidic carboxylic polymers of acrylic acid cross-linked with about 0.75 to about 2.0% of a cross-linking agent of polyallyl sucrose or polyallyl pentaerythritol.

The oral compositions of the present invention also include products which are substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of the oral compositions of the present invention is generally in the range of from about 4.5 to about 9 preferably in the range of from about 6 to about 8.0. The pH can be controlled with acid (e.g., citric acid or benzoic acid) or base (e.g., sodium hydroxide) or buffered (as with sodium citrate, benzoate, carbonate, or bicarbonate, disodium hydrogen phosphate, sodium dihydrogen phosphate, etc.).

In certain preferred forms of this invention, fluorine-providing salts having anti-caries efficacy may be incorporated in the oral compositions and are characterized by their ability to release fluoride ions in water. Among these materials are inorganic metal salts, for example, sodium fluoride, potassium fluoride, cuprous fluoride, a tin fluoride such as stannous fluoride or stannous chlorofluoride, sodium fluorosilicate, ammonium fluorosilicate, sodium monofluorophosphate, alumina mono-and difluorophosphate.

The amount of the fluoride-providing compound is dependent to some extent upon the type of compound, its solubility, and the type of oral preparation, but it must be a nontoxic amount, generally about 0.01 to about 3.0% in the composition. In a solid oral composition such as a gel, toothpaste or cream, an amount of such fluoride providing compound which releases up to about 1% F ion by weight of the preparation is considered satisfactory. Any suitable minimum amount of such compound may be used, but it is preferable to employ sufficient fluoride compound to release about 0.005% to 1%, more preferably about 0.1% of fluoride ion. Typically, in the cases of alkali metal fluorides and stannous fluoride, this component is present in an amount up to about 25% by weight, based on the weight of the preparation, and preferably in the range of about 0.05% to 1%. In the case of sodium monofluorophosphate, the compound may be present in an amount of about 0.1–3.0%.

In a liquid oral preparation such as a mouthwash or rinse, the fluoride-providing compound is typically present in an amount sufficient to release up to about 1.0%, preferably about 0.001% to 0.5% by weight of fluoride ion. Generally, about 0.01 to about 3.0 wt. % of such compound is present.

Pyrophosphate salts having anti-tartar efficacy such as a dialkali or tetra-alkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphates such as sodium trimetaphosphate are incorporated in solid oral compositions of the present invention preferably at a concentration of about 0.5 to about 8.0% by weight. In liquid oral preparations, the pyrophosphate salts are incorporated at a concentration of about 0.1 to about 3% by weight.

Antibacterial agents may also be included in the oral compositions of the present invention. Especially useful are non-cationic antibacterial agents which are based on phenolic and bisphenolic compounds, halogenated diphenyl ether, benzoate esters and carbanilides. Examples of such compounds are 4-chlorophenol, 2,2'-trichloro-2-hydroxy-diphenyl ether (Triclosan), esters of p-hydroxybenzoic acid, especially methyl, ethyl, propyl, butyl and benzyl esters, 3, 4, 4'-trichlorocarbanalide and 3, 3', 4-trichlorocarbanilide. Triclosan in amounts ranging from 0.03% to 1% is preferred for use in the compositions of the present invention.

Nonionic antimicrobial agents such as sesquiterpene alcohols such as merolidol and bisabolol are also useful in the present invention.

Tooth whitening agents may also be included in the oral compositions of the present invention. Especially useful are oxidizing agents such as calcium peroxide, sodium perborate, hydrogen peroxide, urea peroxide, peracetic acid, sodium percarbonate or any other source that, in aqueous solutions, acts as an hydrogen peroxide source. The amount of active oxygen in such oral compositions can vary from 0.7% to 5% by weight and preferably about 0.5% to about 2% by weight.

The oral composition of the present invention may be prepared by suitably mixing the ingredients. In the preparation of a solid composition such as a toothpaste, a thickener such as carboxymethyl cellulose or hydroxyethyl cellulose is dispersed with a humectant, water, salts such as tetrasodium pyrophosphate, sodium fluoride or sodium monofluorophosphate, and sweetener such as saccharin are then added and mixed. A polishing agent such as dicalcium phosphate, purified sodium lauryl sulfoacetate surfactant, foam enhancing compounds and flavor are then added. The ingredients are then mixed under vacuum for about 15–30 minutes. The resulting gel or paste is then tubed.

The following examples are further illustrative of the present invention, but it is understood that the invention is not limited thereto. All amounts and proportions referred to herein and in the appended claims are by weight unless otherwise indicated.

EXAMPLE I

A toothpaste was prepared having the composition of Table I

TABLE I

| INGREDIENTS | Wt % |
|---|---|
| Dicalcium phosphate | 48.00 |
| Glycerine | 18.00 |
| Sorbitol | 6.00 |
| Sodium lauryl sulfoacetate (purified)* | 1.30 |
| Flavor | 0.95 |
| Sodium monofluorophosphate (MFP) | 0.76 |
| Carboxymethyl cellulose (CMC) | 0.50 |
| Hydroxyethyl cellulose (HEC) | 0.50 |
| Tetrasodium pyrophosphate (TSPP) | 0.25 |
| Na saccharin | 0.20 |
| Sodium Fluoride (NaF) | 0.10 |
| Deionized water | q.s. |

*Analysis of purified sodium lauryl sulfoacetate:

| | wt % |
|---|---|
| dodecyl sodium sulfoacetate | 82–85 min. |
| sodium chloride | 7.5–8.0 max. |
| sodium sulfate | 7.5–8.0 max. |
| sodium sulfoacetate | <4 max. |
| free alcohol | <0.6–0.8 max. |

The composition was prepared by mixing glycerine and sorbitol together with CMC and HEC, then adding TSPP and Na Saccharin, followed by deionized water. The mixture was placed in a double planetary vacuum mixer. Dicalcium phosphate, NaF, MFP, flavor and purified sodium lauryl sulfoacetate were added to the mixture, and the ingredients mixed under vacuum for about 15–20 minutes. A homogeneous paste was obtained which, when evaluated by a taste panel, was found to have a pleasant, nonbitter taste.

To assess the foam-enhancing capabilities of the toothpaste of Table I, an artificial saliva solution was prepared with the following composition:

| COMPOSITION OF ARTIFICIAL SALIVA | |
|---|---|
| INGREDIENT | CONCENTRATION (g/l) |
| $CaCl_2.2H_2O$ | 0.228 |
| $MgCl_2.6H_2O$ | 0.061 |
| NaCl | 1.017 |
| $K_2CO_3.15H_2O$ | 0.603 |
| $NaH_2PO_4.H_2O$ | 0.204 |
| $Na_2HPO_4.7H_2O$ | 0.273 |
| Water | q.s. |
| Conc. HCL | Sufficient to achieve pH 6.9 |

To this solution, 16% by weight dicalcium phosphate dihydrate and 0.3% flavoring agent were added along with 0.4% of purified sodium lauryl sulfoacetate. The concentrations of the resulting test solution correspond to a 1:2 dilution of toothpaste in saliva normally associated with toothpaste in the oral cavity.

In performing the foam test, fifteen ml of the test solution were transferred to a 50 ml sterile centrifuge tube. Six replicates were placed in a 37° C. water bath for approximately 15 minutes. The centrifuge tubes were clamped on to a Burrell Wrist-Action Shaker and were shaken an average of 50 times over a 10 second period. The tubes were displaced over 7.0 cm each cycle. Upper and lower foam levels were recorded on the tubes between 5 and 20 seconds after shaking. The difference in the levels provided a "foam volume" value. Increasing foam values correlate to increasing foamability perceived by consumers using the toothpaste.

A 0.98 correlation was found to exist between the foam test results using diluted toothpaste and the foamability rated by a human test panel brushing with undiluted toothpaste.

The foam volume of the test solution representative of Example I is recorded in Table II below (Run No. 1).

The procedure of Example I was repeated with the exception that a series of test solutions (Run Nos. 2–7) was prepared in which a variety of different nonionic or amphoteric foam enhancing compounds were also included in the test solutions. The concentrations of these additives and the foam volumes of the test solutions are also recorded in Table II.

For purposes of comparison, a solution prepared wherein SLS was substituted for purified sodium lauryl sulfoacetate as the surfactant was also tested for foamability. The foam value of this comparative solution designated "C" is also recorded in Table II.

TABLE II

| Run No. | Foam Enhancing Additive | Additive Concentration (wt %) | Foam Volume (ml) |
|---|---|---|---|
| 1. | None | 0 | 21 |
| 2. | F-108 | 0.10 | 27 |
| 3. | F-127 | 0.10 | 27 |
| 4. | Polyox N60-K | 0.005 | 26 |
| 5.* | Tween 60 | 0.04 | 28 |
| 6. | Allantoin | 0.10 | 29 |
| 7. | Tegobetaine | 0.05 | 29 |
| C | — | 0 | 30 |

*0.36 wt % purified sodium lauryl sulfoacetate

The data in Table II show that, although an oral composition containing purified sodium lauryl sulfoacetate (Run No. 1) exhibits inferior foaming to a similar composition containing SLS (Run C), the presence of a nonionic or amphoteric compound in the solution (Run Nos. 2–7) raises the foaming ability of the oral composition to a level substantially equivalent to that of SLS.

EXAMPLE II

The irritancy of the purified sodium lauryl sulfoacetate surfactant used to prepare the toothpaste compositions of the present invention were evaluated in accordance with the test procedure disclosed in an article entitled "Predicting Surfactant Irritation from the Swelling Response of a Collagen Film," J. Soc. Cosmet, Chem. 37, 199–210 (July/August, 1986). In this test, the swelling (tritriated water uptake) of a collagen film substrate correlates with the irritation of anionic surfactants and products based on these ingredients. Swelling response is concentration dependent and higher substrate swelling indicates greater irritation potential. The results of this in vitro test have been found to correlate with findings from established in vitro and in vivo laboratory and clinical assessments.

In performing the irritancy test, collagen film supplied by Colla-Tec Inc., Plainsboro, N.J., was prepared from bovine deep flexor tendon and cut into 1.27×1.27 cm (0.5×0.5 inch) squares, approximately 10 mg by weight. Each square was placed in a 20-ml screw cap vial and treated with 10 ml solution containing 1% purified sodium lauryl sulfoacetate either alone (Test No. 1) or in combination with a nonionic additive (Tests No. 2–5), and enough tritiated ($^3H_2O$) water to give $1\times10^5$ dpm/ml. The solutions containing the film squares were incubated at 50° C. for 18–24 hours. The film square was then removed from the solution, rinsed in a liter of deionized water for about 5 seconds to remove any adhering tritiated water, and placed in a liquid scintillation vial.

The films were digested in the vials with 1 ml 2N NaOH and dissolved in Ecolume (ICN Biomedicals, Inc.) scintillation cocktail, acidified with 0.25 ml concentrated perchloric acid, and analyzed for radioactivity using a Beckman LS06800 scintillation spectrometer. The swelling was defined as microliters tritiated water taken up per milligram dry collagen (ul/mg). The results are recorded in Table III below.

For purposes of comparison, the irritancy test was repeated with the exception that the irritancy of unpurified sodium lauryl sulfoacetate (Test No. $C_1$) and SLS (Test No. $C_2$) was also determined. Water was used as a control (Test No. $C_3$). The results of these comparative tests are also recorded in Table III below.

TABLE III

| Test No. | Additive | Additive Concentration WT. % | Irritancy Collagen Swelling ul/mg |
|---|---|---|---|
| 1. | None | 0 | 7.44 |
| 2. | Polyox N60-K | 0.20 | 7.10 |
| 3. | Allantoin | 0.20 | 6.58 |
| 4. | PVP K-15 | 0.25 | 5.94 |
| 5. | Pluronic F-108 + F-127 (1:1) | 0.30 | 5.10 |
| $C_1$ | None | 0 | 7.91 |
| $C_2$ | None | 0 | 10–15 |
| $C_3$ | None | 0 | 2.50 |

The results recorded in Table III indicate that purified sodium lauryl sulfoacetate (Test No. 1) is less irritating than unpurified sodium lauryl surfoacetate (Test No. $C_1$) and particularly SLS (Test No. $C_2$) The presence of nonionic additives in combination with the purified sodium lauryl sulfoacetate results in a further appreciable reduction in irritancy (Test Nos. 2–5).

EXAMPLE III

The procedure of Example I was repeated to prepare a toothpaste containing an antibacterial agent, triclosan, having the following ingredients:

TABLE IV

| INGREDIENTS | WT. |
|---|---|
| Dicalcium phosphate | 48.00 |
| Glycerine | 18.00 |
| Sorbitol | 6.00 |
| Sodium lauryl sulfoacetate (purified) | 1.30 |
| Flavor | 0.95 |
| Sodium monofluorophosphate (MFP) | 0.76 |
| Sodium Carboxymethyl cellulose (CMC) | 0.50 |
| Hydroxyethyl cellulose (HEC) | 0.50 |
| Triclosan | 0.30 |
| Na Saccharin | 0.20 |
| Sodium Fluoride (NaF) | 0.10 |
| Deionized water | q.s. |

The toothpaste prepared in Example III, when evaluated by a taste panel, was found to have a pleasant, non-bitter taste.

What is claimed is:

1. A substantially non-irritating oral composition which is a dentifrice toothpaste, gel, dental cream, mouthwash or rinse of an acceptable taste, the composition being comprised of an effective amount of a sodium lauryl sulfoacetate surfactant purified to contain about 18% or less by weight impurities, and is substantially free of bitter tasting impurities as well as oral mucosa irritating sodium lauryl sulfate, the effective amount being a concentration of about 0.5 to about 5.0% by weight at which concentration the purified sodium lauryl sulfoacetate is found unexpectedly not to have the normal bitter taste associated with unpurified commercial sodium lauryl sulfoacetate.

2. The composition of claim i wherein the purified sodium lauryl sulfoacetate surfactant has the following analysis:

| | wt % range |
|---|---|
| dodecyl sodium sulfoacetate | 82.0–85.0 min. |
| sodium chloride | 7.5–8.0 max. |
| sodium sulfate | 7.5–8.0 max. |
| sodium sulfoacetate | <4 max. |
| free alcohol | <0.6–0.8 max. |

3. The composition of claim 1 wherein there is incorporated an amount of a nonionic or amphoteric compound effective to enhance the foaming ability and non-irritancy of the surfactant.

4. The composition of claim 1 wherein the nonionic compound is an ethylene oxide containing polymer or oxygen-containing heterocyclic nitrogen compound.

5. The composition of claim 4 wherein the ethylene oxide containing polymer is present in the oral composition at a concentration of about 0.001 to about 5 % by weight.

6. The composition of claim 4 wherein the ethylene oxide containing polymer is a poly(ethylene oxide) of the formula $H(OCH_2CH_2)_xOH$ having a molecular weight of between 500,000 and 4,000,000.

7. The composition of claim 4 wherein the ethylene oxide containing polymer is a polyoxyethylene polyoxypropylene block copolymer having the formula $HO(C_2H_4O)_b(C_3H_6O)_n(C_2H_5O)_bH$.

8. The composition of claim 4 wherein the ethylene oxide polymer is a polyoxyethylene monoester of sorbitol.

9. The composition of claim 4 wherein the oxygen-containing heterocyclic nitrogen compound is present in the oral composition at a concentration of about 0.01 to about 5% by weight.

10. The composition of claim 4 wherein the oxygen-containing heterocyclic nitrogen compound is polyvinylpyrolidone.

11. The composition of claim 4 wherein the oxygen-containing heterocyclic compound is allantoin.

12. The composition of claim 3 wherein the amphoteric composition is present in the oral composition at a concentration of about 0.001 to about 2% by weight.

13. The composition of claim 3 wherein the amphoteric compound is a betaine compound.

14. The composition of claim 13 wherein the betaine compound is cocoamido propyl betaine.

15. The composition of claim 1 wherein there is incorporated about 0.05% to 1% of a nonionic antibacterial agent.

16. The composition of claim 15 wherein the antibacterial agent is triclosan.

* * * * *